(12) United States Patent
Gharda

(10) Patent No.: US 9,198,421 B2
(45) Date of Patent: Dec. 1, 2015

(54) POLYMORPHISM IN 5-AMINO-1-(2,6-DICHLORO-4-TRIFLUOROMETHYLPHENYL)-3-CYANO-4-TRIFLUORO METHYL SULFINYL PYRAZOLE

(76) Inventor: Keki Hormusji Gharda, Mumbai (IN)

( * ) Notice: Subject to any disclaimer, the term of this patent is extended or adjusted under 35 U.S.C. 154(b) by 179 days.

(21) Appl. No.: 13/979,577

(22) PCT Filed: Jan. 13, 2012

(86) PCT No.: PCT/IN2012/000037
§ 371 (c)(1),
(2), (4) Date: Jul. 12, 2013

(87) PCT Pub. No.: WO2012/095871
PCT Pub. Date: Jul. 19, 2012

(65) Prior Publication Data
US 2013/0303581 A1    Nov. 14, 2013

(30) Foreign Application Priority Data
Jan. 14, 2011    (IN) .......................... 133/MUM/2011

(51) Int. Cl.
*C07D 231/16* (2006.01)
*A01N 43/56* (2006.01)
*A01N 47/02* (2006.01)
*C07D 231/44* (2006.01)

(52) U.S. Cl.
CPC ................ *A01N 43/56* (2013.01); *A01N 47/02* (2013.01); *C07D 231/44* (2013.01)

(58) Field of Classification Search
CPC ............................ C07D 237/04; C07D 231/44
See application file for complete search history.

(56) References Cited

U.S. PATENT DOCUMENTS

| | | | |
|---|---|---|---|
| 5,631,381 | A | 5/1997 | Huang et al. |
| 7,777,052 | B2 | 8/2010 | Gharda et al. |

FOREIGN PATENT DOCUMENTS

| | | |
|---|---|---|
| CN | 1374298 A | 10/2002 |
| CN | 101906073 A | 12/2010 |
| EP | 295117 A1 | 12/1988 |
| EP | 460940 A1 | 12/1991 |
| EP | 484165 A1 | 5/1992 |
| EP | 668269 A1 | 8/1995 |
| EP | 967206 A1 | 12/1999 |
| EP | 1331222 A1 | 7/2003 |
| EP | 1374061 B1 | 11/2005 |
| IN | 552/MUM/2010 | 7/2012 |
| IN | 1589/MUM/2011 | 12/2012 |
| WO | 2007/069254 A2 | 6/2007 |
| WO | 2008/055881 A1 | 5/2008 |
| WO | 2008/055882 A1 | 5/2008 |
| WO | 2008/055883 A1 | 5/2008 |
| WO | 2008/055884 A1 | 5/2008 |

OTHER PUBLICATIONS

Yang, H., Ma, Z., and Wang, S; "A Study on Synthesis of Regent;" Journal of Hebei University of Science and Technology, No. 69, vol. 25; 2004 (3 pages).
International Search Report issued in PCT/IN2012/000037 mailed on Jul. 12, 2012 (4 pages).
J. of Heibei University of Science and Technology, vol. 25 (2), Sum 69 (2004), Dok. Serial No. 1008-1542 (2004) 02-0018-03 (3 pages).

*Primary Examiner* — Michael Barker
*Assistant Examiner* — Karen Cheng
(74) *Attorney, Agent, or Firm* — Osha • Liang LLP

(57) ABSTRACT

The present invention provides novel crystalline polymorphic forms of fipronil and processes for preparing the same. The present invention also provides a pesticidal composition containing a pesticidally effective amount of a crystalline form of fipronil and a method for controlling pests using a pesticidally effective amount of a crystalline form of fipronil or its composition.

9 Claims, 4 Drawing Sheets

POLYMORPHISM IN 5-AMINO-1-(2,6-DICHLORO-4-TRIFLUOROMETHYLPHENYL)-3-CYANO-4-TRIFLUORO METHYL SULFINYL PYRAZOLE

FIELD OF THE INVENTION

The present invention relates to novel crystalline forms of fipronil and processes for preparing the same.

BACKGROUND

Fipronil [5-Amino-1-(2,6-dichloro-4-trifluoromethylphenyl)-3-cyano-4-trifluoro methyl sulfinyl pyrazole] is one of the important fluorine bearing 1-Aryl pyrazole derivatives developed in the recent two decades.

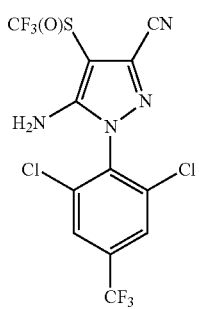

Formula I

It is a broad spectrum insecticide that disrupts central nervous system of insect by blocking the passage of chloride ions through the GABA receptor and glutamate-gated chloride channels (GluCl).

It is mainly used in agriculture fields. Fipronil is particularly applied to soil and seeds to control insects. e.g. fipronil is used to control i) multiple species of thrips on a broad range of crops by foliar, soil or seed treatment, ii) corn rootworm, wireworms and termites by soil treatment in maize, iii) boll weevil and plant bugs on cotton, iv) diamond-back moth on crucifers, v) colorado potato beetle on potatoes by foliar application, vi) stem borers, leaf miners, planthoppers, leaf folder/rollers and weevils in rice.

Various processes for the synthesis of fipronil are described in the following documents:
EP295117; EP460940; EP484165; EP668269; EP967206; EP1331222; EP1374 061; U.S. Pat. No. 5,631,381; CN1374298; and J. of Heibei University of Science and Technology, Vol. 25 (2), Sum 69 (2004), Dok. Serial No. 1008-1542 (2004) 02-0018-03.

The characterization of fipronil is generally carried out by measurement of melting point and by analysis such as IR spectrum, proton & carbon-13 NMR, HPLC, UV and the like.

Polymorphism is the ability of a solid material to exist in more than one form or crystal structure. Typically, when a compound is re-crystallized from a solution or slurry, it may crystallize with different spatial lattice arrangements. The different crystal forms individually are referred as a "polymorph". Different polymorphic forms of a given substance may differ from each other with respect to one or more physical properties, such as solubility and dissociation, true density, crystal shape, compaction behavior, flow properties, and/or solid state stability. Different types of crystalline forms typically affects the manufacturing process such as mixture of two different crystalline forms clog the pores of filters which leads to loss of time and product. Further, it requires tedious and expensive cleaning work. Furthermore, different bulk densities affect the storing and packaging requirements.

Various crystalline modifications of fipronil are disclosed in the following patent documents:

WO2007069254 discloses crystalline polymorph Form I of fipronil which exhibits an X-ray powder diffraction pattern having characteristic peaks expressed in degrees 2θ(+/−0.20° θ) at about 13.04, 16.27, 18.48, 19.65, 22.05, and 31.55. It also discloses crystalline polymorph Form II of fipronil which exhibits an X-ray powder diffraction pattern having characteristic peaks expressed in degrees 2θ(+/−0.20° θ) at about, 14.4, 15.7, 16.75, 17.2, 19, 20.7, 22.95, 23.55, and 32.15.

WO2007069254 also discloses preparation of two types of crystalline polymorphic forms of fipronil. Initially fipronil Pseudomorph is prepared by dissolving fipronil in toluene followed by heating upto 110° C. The obtained Pseudomorph is heated upto 150° C. to form fipronil form III which on exothermic transition get converted to form I. fipronil form II is prepared by dissolving fipronil in isopropyl alcohol or n-hexane or methyl isobutyl ketone followed by heating upto 95° C.

WO2008055881 discloses a crystalline modification I of fipronil showing, in an X-ray powder diffractogram at 30° C., at least 5 of the following reflexes: (1) d=7.45±0.1 A, (2) d=6.07±0.07 A, (3) d=5.57±0.05 A, (4) d=4.84±0.05 A, (5) d=3.76±0.05 A, (6) d=3.67±0.05 A (7) d=3.23±0.05 A, (8) d=3.01±0.05 A and (9) d=2.77±0.05 A. It also discloses preparation of crystalline polymorphic form of fipronil. Fipronil is dissolved in a solvent such as methanol, isopropanol, ethanol, ethyl benzene, diisopropyl benzene, n-butyl benzene, CF3-benzene, acetonitril, DMSO followed by heating.

WO2008055882 discloses a crystalline modification II of fipronil which has an X-ray powder diffractogram showing, at 25° C., at least 5 of the following reflexes: (1) d=13.44±0.2 A, (2) d=7.84±0.1 A, (3) d=5.50±0.07 A, (4) d=5.14±0.05 A (5) d=4.95±0.05 A, (6) d=3.95±0.05 A, (7) d=3.77±0.05 A, (8) d=3.22±0.03 A and (9) d=2.91±0.03 A.

It also discloses a process for preparing the crystalline modification II in which fipronil is dissolved in a solvent selected from tetrahydrofurane, 1,2-dichloroethane, acetonitrile, mono-, di- or tri(Ci-C6-alkyl) benzenes followed by heating upto 137° C.

WO2008055883 discloses a crystalline modification V of fipronil showing, in an X-ray powder diffractogram at 30° C., at least 5 of the following reflexes: (1) d=8.55±0.1 A, (2) d=7.94±0.07 A, (3) d=6.78±0.05 A, (4) d=5.43±0.05 A (5) d=4.35±0.05 A and (6) d=2.83±0.03 A.

It also discloses a process for preparing the crystalline modification V in which a solution of a solid form of fipronil is prepared by dissolving it in a solvent such as dimethylsulfoxide or acetonitrile followed by heating at 60° C. to 150° C.

WO2008055884 discloses a crystalline modification IV of fipronil which has an X-ray powder diffractogram showing, at 30° C., at least 5 of the following reflexes: (1) d=11.28±0.2 A, (2) d=9.04±0.1 A, (3) d=7.61±0.07 A, (4) d=6.46±0.05 A, (5) d=5.28±0.05 A, (6) d=4.59±0.05 A, (7) d=3.59±0.03 A, and (8) d=3.04±0.03 A, It also discloses a process for preparing a crystalline modification IV of fipronil in which a solid form of fipronil is dissolved in acetone followed by crystallization and isolation.

The processes disclosed in the prior art are carried out at higher temperature. Thus there is an urgent and unmet need in the art for an efficient method for the preparation crystalline fipronil, which is simple and can be used on a large scale for industrial manufacture and which produce highly pure product that can be safely utilized.

OBJECTS OF THE INVENTION

It is an object of the present invention to provide novel crystalline forms of Fipronil.

It is another object of the present invention to provide simple and economic processes for preparing crystalline polymorphic forms of Fipronil.

It is still another object of the present invention to provide a process for preparing crystalline polymorphic forms of Fipronil with high yield.

It is yet another object of the present invention to provide a process for crystalline modification of fipronil.

It is still further object of the present invention to elucidate spatial arrangement of a particular polymorph of fipronil.

It is a further object of the present invention to a simple process for converting a polymorph of fipronil into another polymorph of fipronil.

It is another object of the present invention to provide a pesticidal composition containing a pesticidally effective amount of a crystalline form of fipronil.

It is still another object of the present invention to provide a method for controlling pests using a pesticidally effective amount of a crystalline form of fipronil or its composition.

SUMMARY OF THE INVENTION

In accordance with the present invention there is provided a crystalline polymorphic form G of fipronil which, in an X-ray powder diffractogram at 25° C., shows at least 5 of the following reflexes:

| Peak No | 2theta (degrees) | d (Å) |
|---|---|---|
| 1 | 6.15 | 14.36 |
| 2 | 8.37 | 10.56 |
| 3 | 11.31 | 7.82 |
| 4 | 12.16 | 7.27 |
| 5 | 12.84 | 6.89 |
| 6 | 18.22 | 4.87 |
| 7 | 19.07 | 4.65 |
| 8 | 20.82 | 4.26 |
| 9 | 24.93 | 3.57 |
| 10 | 25.65 | 3.47 |
| 11 | 26.32 | 3.38 |
| 12 | 28.96 | 3.08 |

Typically, the fipronil content in crystalline polymorphic form G of fipronil is at least 98% by mass.

In accordance with the another aspect of the present invention there is provided a process for the preparation of a crystalline polymorphic form G of fipronil; said process comprising dissolving solid form of fipronil being different from the crystalline polymorphic form G in dichloromethane to obtain a mixture and subjecting the mixture to column chromatography followed by concentrating and vacuum drying at 30 to 35° C.

Typically, the solid form of fipronil contains at least 81% of fipronil by mass.

In accordance with still another aspect of the present invention there is provided a crystalline polymorphic form XI of fipronil which, in an X-ray powder diffractogram at 25° C., shows at least 5 of the following reflexes:

| Peak No. | 2 theta (degrees) | d (Å) |
|---|---|---|
| 1 | 11.78 | 7.51 |
| 2 | 14.49 | 6.11 |
| 3 | 15.84 | 5.59 |
| 4 | 18.27 | 4.85 |
| 5 | 18.97 | 4.67 |
| 6 | 21.74 | 4.08 |
| 7 | 22.97 | 3.87 |
| 8 | 23.55 | 3.77 |
| 9 | 24.16 | 3.68 |
| 10 | 24.68 | 3.60 |
| 11 | 27.45 | 3.25 |
| 12 | 29.55 | 3.02 |
| 13 | 32.18 | 2.78 |

Typically, the crystalline polymorphic form XI of fipronil is characterized by crystallographic molecular structure as shown in FIG. 4, with the following bond lengths and angles:

| Bond | lengths [Å] |
|---|---|
| S(1)—O(1) | 1.484(2) |
| S(1)—C(2) | 1.740(3) |
| S(1)—C(12) | 1.855(3) |
| Cl(1)—C(6) | 1.725(3) |
| Cl(2)—C(10) | 1.726(3) |
| F(1)—C(11) | 1.278(4) |
| F(2)—C(11) | 1.292(4) |
| F(3)—C(11) | 1.295(4) |
| F(4)—C(12) | 1.322(3) |
| F(5)—C(12) | 1.326(4) |
| F(6)—C(12) | 1.326(4) |
| N(1)—C(3) | 1.314(4) |
| N(1)—N(2) | 1.372(3) |
| N(1)—H(1N) | 0.8800 |
| N(2)—C(1) | 1.357(3) |
| N(2)—C(5) | 1.422(3) |
| N(3)—C(1) | 1.335(4) |
| N(3)—H(3N) | 0.85(4) |
| N(3)—H(4N) | 0.79(4) |
| N(4)—C(4) | 1.141(4) |
| C(1)—C(2) | 1.399(4) |
| C(2)—C(3) | 1.415(4) |
| C(3)—C(4) | 1.439(4) |
| C(5)—C(10) | 1.387(4) |
| C(5)—C(6) | 1.392(4) |
| C(6)—C(7) | 1.384(4) |
| C(7)—C(8) | 1.383(4) |
| C(7)—H(7) | 0.9500 |
| C(8)—C(9) | 1.383(4) |
| C(8)—C(11) | 1.505(4) |
| C(9)—C(10) | 1.384(4) |
| C(9)—H(9) | 0.9500 |
| | angles [deg] |
| O(1)—S(1)—C(2) | 108.40(12) |
| O(1)—S(1)—C(12) | 102.86(13) |
| C(2)—S(1)—C(12) | 96.02(14) |
| C(3)—N(1)—N(2) | 103.9(2) |
| C(3)—N(1)—H(1N) | 128.1 |
| N(2)—N(1)—H(1N) | 128.1 |
| C(1)—N(2)—N(1) | 113.5(2) |
| C(1)—N(2)—C(5) | 125.1(2) |
| N(1)—N(2)—C(5) | 120.0(2) |
| C(1)—N(3)—H(3N) | 118(2) |
| C(1)—N(3)—H(4N) | 117(2) |
| H(3N)—N(3)—H(4N) | 120(3) |
| N(3)—C(1)—N(2) | 122.9(2) |
| N(3)—C(1)—C(2) | 131.9(3) |
| N(2)—C(1)—C(2) | 105.2(2) |
| C(1)—C(2)—C(3) | 104.6(2) |
| C(1)—C(2)—S(1) | 127.2(2) |
| C(3)—C(2)—S(1) | 128.1(2) |
| N(1)—C(3)—C(2) | 112.8(2) |
| N(1)—C(3)—C(4) | 119.5(2) |

-continued

| Bond | |
|---|---|
| C(2)—C(3)—C(4) | 127.7(2) |
| N(4)—C(4)—C(3) | 179.1(4) |
| C(10)—C(5)—C(6) | 119.4(2) |
| C(10)—C(5)—N(2) | 119.3(2) |
| C(6)—C(5)—N(2) | 121.3(2) |
| C(7)—C(6)—C(5) | 120.6(2) |
| C(7)—C(6)—Cl(1) | 119.7(2) |
| C(5)—C(6)—Cl(1) | 119.7(2) |
| C(8)—C(7)—C(6) | 118.7(3) |
| C(8)—C(7)—H(7) | 120.7 |
| C(6)—C(7)—H(7) | 120.7 |
| C(7)—C(8)—C(9) | 121.8(3) |
| C(7)—C(8)—C(11) | 119.3(3) |
| C(9)—C(8)—C(11) | 118.9(3) |
| C(8)—C(9)—C(10) | 118.7(3) |
| C(8)—C(9)—H(9) | 120.6 |
| C(10)—C(9)—H(9) | 120.6 |
| C(9)—C(10)—C(5) | 120.7(2) |
| C(9)—C(10)—Cl(2) | 119.4(2) |
| C(5)—C(10)—Cl(2) | 119.9(2) |
| F(1)—C(11)—F(2) | 107.6(4) |
| F(1)—C(11)—F(3) | 105.6(3) |
| F(2)—C(11)—F(3) | 104.8(4) |
| F(1)—C(11)—C(8) | 112.5(3) |
| F(2)—C(11)—C(8) | 112.3(3) |
| F(3)—C(11)—C(8) | 113.5(3) |
| F(4)—C(12)—F(6) | 107.9(2) |
| F(4)—C(12)—F(5) | 108.5(3) |
| F(6)—C(12)—F(5) | 108.7(2) |
| F(4)—C(12)—S(1) | 112.63(19) |
| F(6)—C(12)—S(1) | 109.3(2) |
| F(5)—C(12)—S(1) | 109.8(2) |

In accordance with yet another aspect of the present invention there is provided a process for the preparation of a crystalline polymorphic form XI of fipronil; said process comprising heating a crystalline polymorphic form G of fipronil at 140° C.

In accordance with a further aspect of the present invention there is provided a crystalline polymorphic form X of fipronil which, in an X-ray powder diffractogram at 25° C., shows at least 5 of the following reflexes:

| Peak No. | 2 theta (degrees) | d (Å) |
|---|---|---|
| 1 | 6.49 | 13.61 |
| 2 | 11.19 | 7.90 |
| 3 | 16.04 | 5.52 |
| 4 | 16.60 | 5.34 |
| 5 | 17.20 | 5.15 |
| 6 | 17.86 | 4.96 |
| 7 | 18.98 | 4.67 |
| 8 | 19.61 | 4.52 |
| 9 | 20.70 | 4.29 |
| 10 | 22.11 | 4.02 |
| 11 | 22.45 | 3.96 |
| 12 | 23.31 | 3.81 |
| 13 | 25.00 | 3.56 |
| 14 | 26.17 | 3.40 |
| 15 | 26.74 | 3.33 |
| 16 | 27.63 | 3.23 |
| 17 | 28.37 | 3.14 |
| 18 | 29.72 | 3.00 |
| 19 | 30.01 | 2.98 |
| 20 | 30.84 | 2.90 |
| 21 | 32.23 | 2.78 |
| 22 | 32.84 | 2.73 |
| 23 | 34.06 | 2.63 |

In accordance with still further aspect of the present invention there is provided a process for the preparation of a crystalline polymorphic form X of fipronil; said process comprising the following steps:

dissolving fipronil form XI in a solvent mixture comprising monochlorobenzene and ethyl acetate to obtain a mixture;

heating the mixture at a temperature of about 80° C. to obtain a clear solution;

stirring the clear solution for a period of about one hour to obtain a stirred solution;

cooling the stirred solution at ambient temperature, and isolating a crystalline polymorphic form X by evaporating the solvent followed by drying at a temperature of about 60° C. for a period of about 8 to about 10 hours.

In accordance with another aspect of the present invention there is provided a pesticidal composition comprising i) a pesticidally effective amount of at least one crystalline form of fipronil selected from the group consisting of form G, form X and form XI; and ii) at least one excipient.

Typically, the composition is in a form selected from the group consisting of spray, solution, gel, suspension, granules and powder.

In accordance with still another aspect of the present invention there is provided a method for controlling pests; said method comprising contacting the pests or their food supply, habitat, breeding grounds or their locus with a pesticidally effective amount of a composition of the present invention.

In accordance with yet another aspect of the present invention there is provided a method for protecting a plant from infestation and attack by pests; said method comprising applying a pesticidally effective amount of a composition of the present invention to at least one plant part selected from the group consisting of foliage and stem.

In accordance with a further aspect of the present invention there is provided a method of protection of seeds; said method comprises contacting seeds with a pesticidally effective amount of a composition of the present invention.

BRIEF DESCRIPTION OF THE ACCOMPANYING DRAWINGS

The invention will now be described with reference to the accompanying drawings in which.

DETAILED DESCRIPTION OF THE INVENTION

Figure 1:
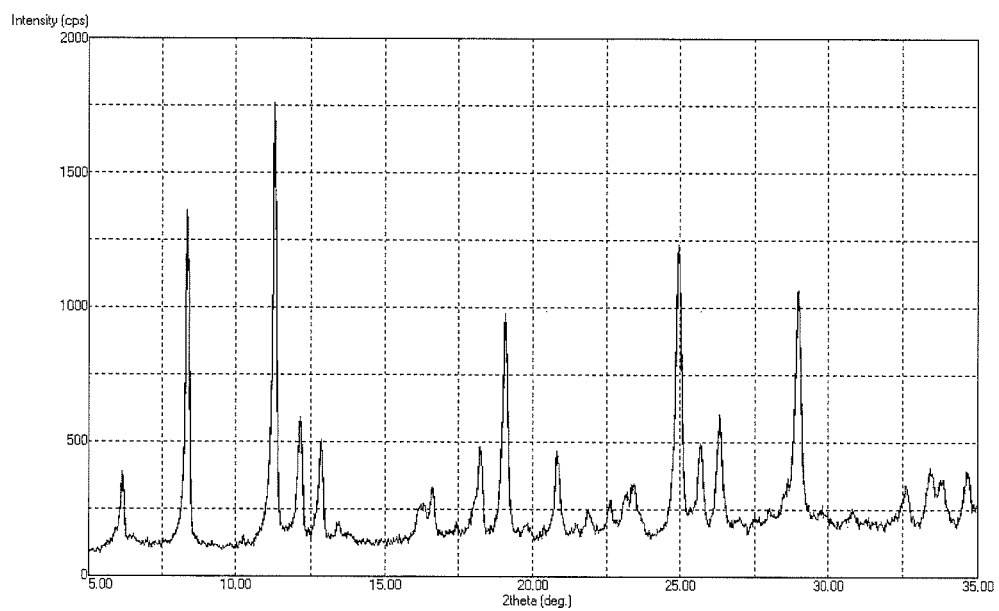
FIG. 1 illustrates X-ray powder diffractogram of crystalline polymorphic form G of fipronil.
Figure 2:
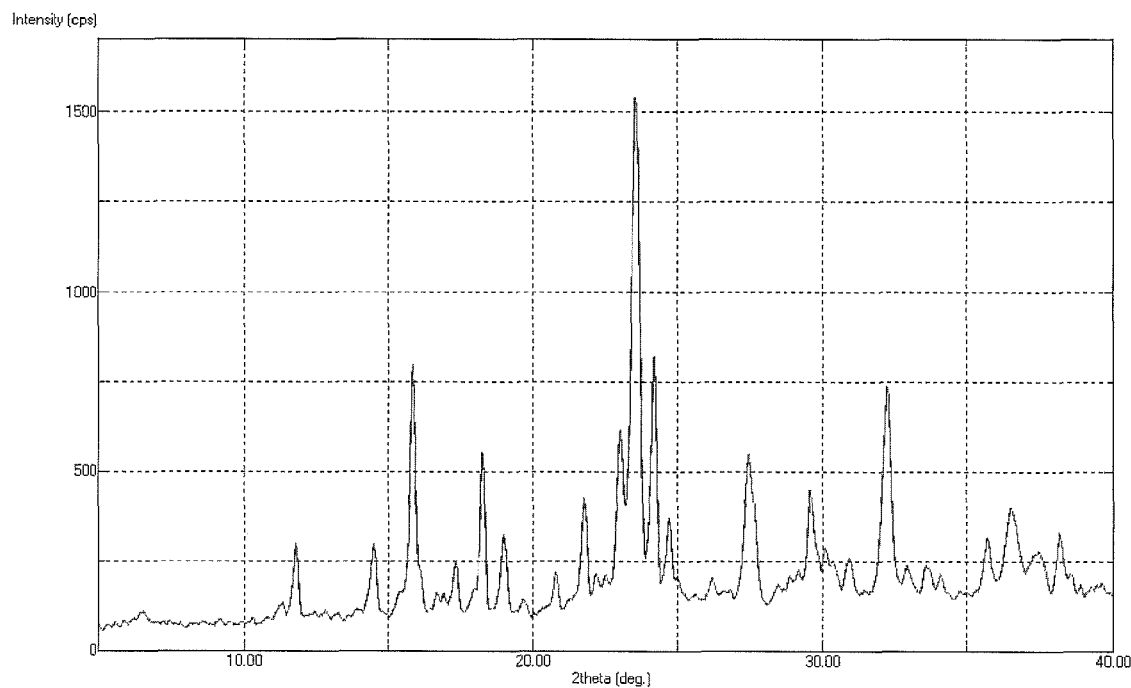
FIG. 2 illustrates X-ray powder diffractogram of crystalline polymorphic form XI of fipronil.
Figure 3:
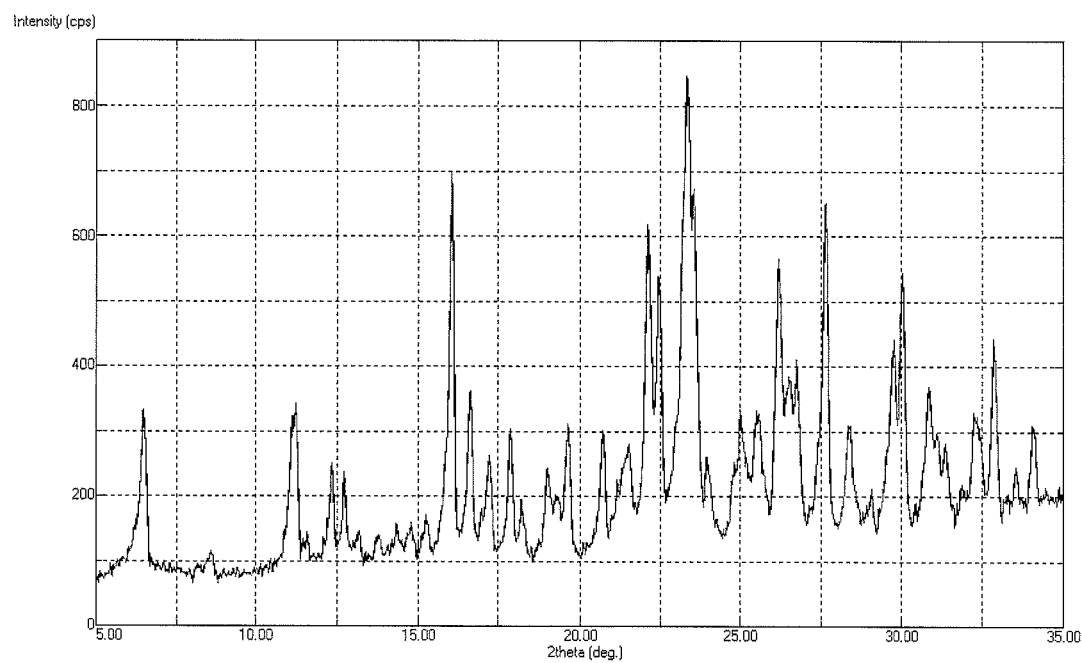
FIG. 3 illustrates X-ray powder diffractogram of crystalline polymorphic form X of fipronil.

The present invention is directed to novel crystalline polymorphic forms of fipronil (5-amino-1-[2,6-dichloro-4-(trifluoromethyl)phenyl]-4-[(trifluoromethyl)sulfinyl]-1H-pyrazole-3-carbonitrile).

The inventors of the present invention, after extensive experimentation, developed simple processes for preparing crystalline forms of fipornil. Furthermore, the inventors of the present invention found three novel crystalline forms of 5-amino-1-[2,6-dichloro-4-(trifluoromethyl)phenyl]-4-[(trifluoromethyl)sulfinyl]-1H-pyrazole-3-carbonitrile (fipronil), designated form G, form XI and form X.

These new Forms exhibit different spectral characteristics as depicted by their distinct X-ray diffraction patterns.

Initially, fipronil is prepared by an oxidation method as disclosed in the U.S. Pat. No. 7,777,052, 552/MUM/2010 or 1589/MUM/2011. The obtained fipronil is purified to obtain a solid form of fipronil containing at least 81% of fipronil by mass. Then solid form of fipronil is converted to a crystalline polymorphic form G of fipronil.

The process for obtaining a crystalline polymorphic form G of fipronil in accordance with the present invention is described herein below:

Initially, solid form of fipronil being different from the crystalline polymorphic form G is dissolved in dichloromethane to obtain a mixture. The mixture is then subjected to column chromatography followed by concentrating and vacuum drying at 30 to 35° C. to obtain a crystalline polymorphic form G of fipronil. Silica ($SiO_2$) or alumina ($Al_2O_3$) of size about 50 to about 300 mesh is used in column chromatography as an adsorbent or as a stationary phase.

The fipronil content in crystalline polymorphic form G of fipronil is at least 98% by mass.

The crystalline polymorphic form G of fipronil obtained by the process of the present invention is checked for X-ray powder diffraction analysis at 25° C. The solid fipronil powder (form G) exhibited the following X-ray diffraction pattern having characteristic peaks at angles expressed in degrees, $2\theta(+/-0.2)$ and inter-planar spacing expressed in Å, d (+/− 0.1) values.

| Peaks | 2theta (degrees) | Peaks | d (Å) |
|---|---|---|---|
| 1 | 6.15 | 1 | 14.36 |
| 2 | 8.37 | 2 | 10.56 |
| 3 | 11.31 | 3 | 7.82 |
| 4 | 12.16 | 4 | 7.27 |
| 5 | 12.84 | 5 | 6.89 |
| 6 | 16.10 | 6 | 5.50 |
| 7 | 16.59 | 7 | 5.34 |
| 8 | 18.22 | 8 | 4.87 |
| 9 | 19.07 | 9 | 4.65 |
| 10 | 20.83 | 10 | 4.26 |
| 11 | 23.11 | 11 | 3.85 |
| 12 | 23.42 | 12 | 3.80 |
| 13 | 24.93 | 13 | 3.57 |
| 14 | 25.67 | 14 | 3.47 |
| 15 | 26.31 | 15 | 3.38 |
| 16 | 28.96 | 16 | 3.08 |
| 17 | 32.60 | 17 | 2.74 |
| 18 | 33.39 | 18 | 2.68 |
| 19 | 33.73 | 19 | 2.66 |
| 20 | 33.86 | 20 | 2.65 |
| 21 | 34.67 | 21 | 2.59 |

The inventors of the present invention further prepared a crystalline polymorphic form XI of fipronil from the crystalline polymorphic form G of fipronil by heating the polymorphic form G of fipronil at 140° C.

The crystalline polymorphic form XI of fipronil prepared in accordance with the present invention, in an X-ray powder diffractogram at 25° C., shows at least 5 of the following reflexes:

| Peak No. | 2 theta (degrees) | d (Å) |
|---|---|---|
| 1 | 11.78 | 7.51 |
| 2 | 14.49 | 6.11 |
| 3 | 15.84 | 5.59 |
| 4 | 18.27 | 4.85 |
| 5 | 18.97 | 4.67 |
| 6 | 21.74 | 4.08 |
| 7 | 22.97 | 3.87 |
| 8 | 23.55 | 3.77 |
| 9 | 24.16 | 3.68 |
| 10 | 24.68 | 3.60 |
| 11 | 27.45 | 3.25 |
| 12 | 29.55 | 3.02 |
| 13 | 32.18 | 2.78 |

Further, the three dimensional crystallographic structure of fipronil Form XI which is hitherto unknown, was determined by single crystal analysis under the following conditions:

| | |
|---|---|
| Ambient temperature | 150(2) K |
| Radiation type, wavelength | Mo K\a, 0.71073 |
| Radiation source | 'Enhance (Mo) X-ray Source' |
| Radiation monochromator | Graphite |

X-Ray Crystallography

Single crystal X-ray structural studies of Fipronil form XI were performed on a CCD Oxford Diffraction XCALIBUR-S diffractometer equipped with an Oxford Instruments low-temperature attachment. Data were collected at 150(2) K using graphite-monochromoated Mo Kα radiation ($\lambda_\alpha$=0.71073 Å). The strategy for the Data collection was evaluated by using the CrysAlisPro CCD software. The data were collected by the standard 'phi-omega scan techniques, and were scaled and reduced using CrysAlisPro RED software. The structures were solved by direct methods using SHELXS-97 and refined by full matrix least-squares with SHELXL-97, refining on $F^2$.

The positions of all the atoms were obtained by direct methods. All non-hydrogen atoms were refined anisotropically. The remaining hydrogen atoms were placed in geometrically constrained positions and refined with isotropic temperature factors, generally 1.2 $U_{eq}$ of their parent atoms. The crystal and refinement data are summarized in Table No. 1

TABLE 1

Crystal data and structure refinement for fipronil

| | |
|---|---|
| Empirical formula | C12H5Cl2F6N4OS |
| Formula weight | 438.16 |
| Temperature | 150(2) K |
| Wavelength | 0.71073 A |
| Crystal system, space group | Monoclinic, C 2/c |
| Unit cell dimensions | a = 22.5215(16) A   alpha = 90 deg. |
| | b = 12.6859(2) A    beta = 138.896(14) deg. |
| | c = 17.3767(13) A   gamma = 90 deg. |
| Volume | 3263.9(3) $A^3$ |
| Z, Calculated density | 8, 1.783 $Mg/m^3$ |
| Absorption coefficient | 0.600 $mm^{-1}$ |
| F(000) | 1736 |
| Crystal size | 0.34 × 0.30 × 0.26 mm |
| Theta range for data collection | 3.37 to 24.99 deg. |
| Limiting indices | −26 <= h <= 26, −15 <= k <= 15, −20 <= l <= 20 |
| Reflections collected/unique | 11626/2873 [R(int) = 0.0214] |
| Completeness to theta = 25.00 | 99.8% |
| Absorption correction | Semi-empirical from equivalents |
| Max. and min. transmission | 0.8595 and 0.8219 |
| Refinement method | Full-matrix least-squares on $F^2$ |
| Data/restraints/parameters | 2873/0/243 |
| Goodness-of-fit on $F^2$ | 1.061 |
| Final R indices [I > 2sigma(I)] | R1 = 0.0415, wR2 = 0.1084 |

TABLE 1-continued

Crystal data and structure refinement for fipronil

| | |
|---|---|
| R indices (all data) | R1 = 0.0456, wR2 = 0.1104 |
| Largest diff. peak and hole | 0.928 and −0.754 e · A$^{-3}$ | a, b, c = Length of unit cell edges
α, β, γ = Angles of the unit cell
Z = Number of molecules in the unit cell.

Figure 4:
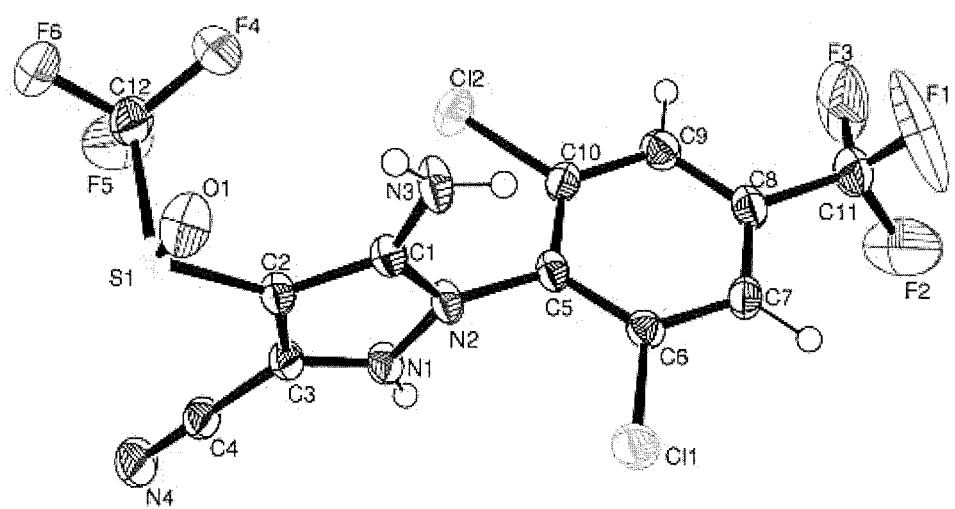
FIG. 4 illustrates crystallographic structure of polymorphic form XI of fipronil.

The crystalline polymorphic form XI of fipronil is characterized by crystallographic molecular structure as shown in FIG. 4, with the following bond lengths and angles:

| Bond | lengths [Å] |
|---|---|
| S(1)—O(1) | 1.484(2) |
| S(1)—C(2) | 1.740(3) |
| S(1)—C(12) | 1.855(3) |
| Cl(1)—C(6) | 1.725(3) |
| Cl(2)—C(10) | 1.726(3) |
| F(1)—C(11) | 1.278(4) |
| F(2)—C(11) | 1.292(4) |
| F(3)—C(11) | 1.295(4) |
| F(4)—C(12) | 1.322(3) |
| F(5)—C(12) | 1.326(4) |
| F(6)—C(12) | 1.326(4) |
| N(1)—C(3) | 1.314(4) |
| N(1)—N(2) | 1.372(3) |
| N(1)—H(1N) | 0.8800 |
| N(2)—C(1) | 1.357(3) |
| N(2)—C(5) | 1.422(3) |
| N(3)—C(1) | 1.335(4) |
| N(3)—H(3N) | 0.85(4) |
| N(3)—H(4N) | 0.79(4) |
| N(4)—C(4) | 1.141(4) |
| C(1)—C(2) | 1.399(4) |
| C(2)—C(3) | 1.415(4) |
| C(3)—C(4) | 1.439(4) |
| C(5)—C(10) | 1.387(4) |
| C(5)—C(6) | 1.392(4) |
| C(6)—C(7) | 1.384(4) |
| C(7)—C(8) | 1.383(4) |
| C(7)—H(7) | 0.9500 |
| C(8)—C(9) | 1.383(4) |
| C(8)—C(11) | 1.505(4) |
| C(9)—C(10) | 1.384(4) |
| C(9)—H(9) | 0.9500 |

| Bond | angles [deg] |
|---|---|
| O(1)—S(1)—C(2) | 108.40(12) |
| O(1)—S(1)—C(12) | 102.86(13) |
| C(2)—S(1)—C(12) | 96.02(14) |
| C(3)—N(1)—N(2) | 103.9(2) |
| C(3)—N(1)—H(1N) | 128.1 |
| N(2)—N(1)—H(1N) | 128.1 |
| C(1)—N(2)—N(1) | 113.5(2) |
| C(1)—N(2)—C(5) | 125.1(2) |
| N(1)—N(2)—C(5) | 120.0(2) |
| C(1)—N(3)—H(3N) | 118(2) |
| C(1)—N(3)—H(4N) | 117(2) |
| H(3N)—N(3)—H(4N) | 120(3) |
| N(3)—C(1)—N(2) | 122.9(2) |
| N(3)—C(1)—C(2) | 131.9(3) |
| N(2)—C(1)—C(2) | 105.2(2) |
| C(1)—C(2)—C(3) | 104.6(2) |
| C(1)—C(2)—S(1) | 127.2(2) |
| C(3)—C(2)—S(1) | 128.1(2) |
| N(1)—C(3)—C(2) | 112.8(2) |
| N(1)—C(3)—C(4) | 119.5(2) |
| C(2)—C(3)—C(4) | 127.7(2) |
| N(4)—C(4)—C(3) | 179.1(4) |
| C(10)—C(5)—C(6) | 119.4(2) |
| C(10)—C(5)—N(2) | 119.3(2) |
| C(6)—C(5)—N(2) | 121.3(2) |
| C(7)—C(6)—C(5) | 120.6(2) |
| C(7)—C(6)—Cl(1) | 119.7(2) |
| C(5)—C(6)—Cl(1) | 119.7(2) |
| C(8)—C(7)—C(6) | 118.7(3) |
| C(8)—C(7)—H(7) | 120.7 |
| C(6)—C(7)—H(7) | 120.7 |
| C(7)—C(8)—C(9) | 121.8(3) |
| C(7)—C(8)—C(11) | 119.3(3) |
| C(9)—C(8)—C(11) | 118.9(3) |
| C(8)—C(9)—C(10) | 118.7(3) |
| C(8)—C(9)—H(9) | 120.6 |
| C(10)—C(9)—H(9) | 120.6 |
| C(9)—C(10)—C(5) | 120.7(2) |
| C(9)—C(10)—Cl(2) | 119.4(2) |
| C(5)—C(10)—Cl(2) | 119.9(2) |
| F(1)—C(11)—F(2) | 107.6(4) |
| F(1)—C(11)—F(3) | 105.6(3) |
| F(2)—C(11)—F(3) | 104.8(4) |
| F(1)—C(11)—C(8) | 112.5(3) |
| F(2)—C(11)—C(8) | 112.3(3) |
| F(3)—C(11)—C(8) | 113.5(3) |
| F(4)—C(12)—F(6) | 107.9(2) |
| F(4)—C(12)—F(5) | 108.5(3) |
| F(6)—C(12)—F(5) | 108.7(2) |
| F(4)—C(12)—S(1) | 112.63(19) |
| F(6)—C(12)—S(1) | 109.3(2) |
| F(5)—C(12)—S(1) | 109.8(2) |

Furthermore, the inventors of the present invention prepared a crystalline polymorphic form X of fipronil from the crystalline polymorphic form XI. The process is described herein below:

In the first step, fipronil form XI is dissolved in a solvent mixture comprising monochlorobenzene and ethyl acetate to obtain a mixture. The obtained mixture is then heated at a temperature of about 80° C. to obtain a clear solution which is then stirred for a period of about one hour to obtain a stirred solution. The stirred solution is cooled at ambient temperature. A crystalline polymorphic form X is then isolated by evaporating the solvent followed by drying at a temperature of about 60° C. for a period of about 8 to about 10 hours.

The crystalline polymorphic form X of fipronil prepared in accordance with the present invention, in an X-ray powder diffractogram at 25° C., shows at least 5 of the following reflexes:

| Peak No. | 2 theta (degrees) | d (Å) |
|---|---|---|
| 1 | 6.49 | 13.61 |
| 2 | 11.19 | 7.90 |
| 3 | 16.04 | 5.52 |
| 4 | 16.60 | 5.34 |
| 5 | 17.20 | 5.15 |
| 6 | 17.86 | 4.96 |
| 7 | 18.98 | 4.67 |
| 8 | 19.61 | 4.52 |
| 9 | 20.70 | 4.29 |
| 10 | 22.11 | 4.02 |
| 11 | 22.45 | 3.96 |
| 12 | 23.31 | 3.81 |
| 13 | 25.00 | 3.56 |
| 14 | 26.17 | 3.40 |
| 15 | 26.74 | 3.33 |
| 16 | 27.63 | 3.23 |
| 17 | 28.37 | 3.14 |
| 18 | 29.72 | 3.00 |
| 19 | 30.01 | 2.98 |
| 20 | 30.84 | 2.90 |
| 21 | 32.23 | 2.78 |
| 22 | 32.84 | 2.73 |
| 23 | 34.06 | 2.63 |

The inventors of the present invention further prepared a pesticidal composition by using novel crystalline forms of fipronil as obtained by the present invention. The prepared pesticidal composition contains a pesticidally effective amount of at least one crystalline form of fipronil selected from the group consisting of form G, form X and form XI; and ii) at least one excipient. The composition is then converted to a form which includes but is not limited to spray, solution, gel, suspension, granules and powder.

The excipients used for the preparation of pesticidal formulations in accordance with the present invention include but are not limited to surfactants, anti-foam agents, thickeners, wetting agents, binding agents, dispersing agents, penetrating agents, anti-freezing agents, pH adjusting agents, preservatives, sweetening agents, vehicles, stabilizers and the like.

The surfactants used for the preparation of formulations in accordance with present invention include but are not limited to anionic surfactants and nonionic surfactants.

The anionic surfactants include alkylaryl sulfonates, phenyl sulfonates, alkyl sulfates, alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol, alkyl phosphates, alkylaryl phosphates, polyacrylates, maleic anhydride and mixtures thereof.

Examples of nonionic surfactants include alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof.

Antifoam agents suitable for the preparation of formulations in accordance with present invention include but are not limited to silicone emulsions, long-chain alcohols, fatty acids, organofluorine compounds and mixtures thereof.

Viscosity-modifying additives (thickeners) suitable for the preparation formulations in accordance with present invention include but are not limited to hydroxypropyl methylcellulose, hydroxypropyl cellulose, sodium carboxy methyl cellulose, hydroxyethyl cellulose, carbopol polyethylene glycol, acrylates, methacrylates, gelatin, alginates, pectins, tragacanth, karaya gum, xanthan gum, carrageenin, agar, alginate, chitosan, bento-nites, attapulgites and acacia.

Wetting agent used for the preparation of formulations in accordance with present invention include but is not limited to naphthalenesulfonic acids, fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates, fatty acid polyglycol esters, phenyl naphthalene sulphonates, alkyl naphthalene sulfonates, sodium alkyl naphthalene sulfonate, sodium salt of sulfonated alkylcarboxylate, polyoxyalkylated ethyl phenols, polyoxyethoylated fatty alcohols, polyoxyethoxylated fatty amines, lignin derivatives, alkane sulfonates, alkylbenzene sulfonates, salts of polycarboxylic acids, salts of esters of sulfosuccinic acid, alkylnaphthalenesulphonates, alkylbenzenesulfonates, alkylpolyglycol ether sulfonates, alkyl ether phosphates, alkyl ether sulphates and alkyl sulfosuccinic monoesters.

The binding agent is selected from the group consisting of bentonite, gypsum, starch, pregelatinized starch, gelatin, vinyl chloride, povidone, hydroxylpropyl cellulose, ethyl cellulose, xanthan gum, cellulose acetate phthalate, hydroxyl propyl methyl cellulos, polyvinyl alcohols, phenyl naphthalene sulphonate, lignin derivatives, polyvinyl pyrrolidone, polyalkylpyrrolidone, polyethoxylated fatty acids, polyethoxylated fatty alcohols, ethylene oxide copolymer, propylene oxide copolymer, polyethylene glycols and polyethylene oxides.

In accordance with present invention buffer (pH adjusting agent) is used for regulating the pH. Examples of buffers are alkali metal salts of weak inorganic or organic acids, such as phosphoric acid, boric acid, acetic acid, propionic acid, citric acid, fumaric acid, tartaric acid, oxalic acid and succinic acid.

The present invention also provides a method for controlling pests. The method involves contacting the pests or their food supply, habitat, breeding grounds or their locus with a pesticidally effective amount of a composition of the present invention. In one of the embodiments, the composition is in the form gel and is used for controlling household insects such cockroaches, flies and the like.

Further, the present invention also provides a method for protecting a plant from infestation and attack by pests. The method involves application of a pesticidally effective amount of a composition of the present invention to at least one plant part selected from the group consisting of foliage and stem.

Still further, the present invention provides a method of protection of seeds which involves contacting seeds with a pesticidally effective amount of a composition of the present invention.

The present disclosure is further described in light of the following examples which are set forth for illustration purpose only and not to be construed for limiting the scope of the disclosure.

EXAMPLES

Preparation of Fipronil Form G

Example-1

Fipronil (15 gm), (prepared by oxidation of thiopyrazole using trichloro acetic acid, monochlorobenzene and hydrogen peroxide as an oxidizing agent, purity=69.85%, thiopyrazole=28.17%, fipronil sulfone=1.26%) was dissolved in 300 ml. of methylene dichloride (MDC). A column was prepared using 150 gm of Silica (60-120 mesh) using MDC as a solvent. A clear solution of Fipronil was then into the column and elution was done with MDC solvent at ambient temperature. Different products as per bands were separated and TLC analysis was carried out. MDC cut containing Fipronil was concentrated at 30-35° C. under vacuum and the product was isolated. The obtained Fipronil shows 99.22% purity. XRD analysis of the obtained Fipronil shows a new polymorph which is designated as 'G' form.

Example-2

Fipronil (15 gm), (prepared by oxidation of thiopyrazole using 98% $H_2SO_4$, dichloroethane and hydrogen peroxide as an oxidizing agent, purity=78%, thiopyrazole=16.54%, fipronil sulfone=2.46%), was dissolved in 300 ml. of methylene dichloride (MDC). A column was prepared using 150 gm of Silica (60-120 mesh) using MDC as a solvent. A clear solution of Fipronil was added into the column and elution was done with MDC solvent at ambient temperature. Different products as per bands were separated and TLC analysis was carried out. MDC cut containing Fipronil was concentrated at 30-35° C. under vacuum and the product was isolated. The obtained Fipronil shows 99.14% purity. XRD analysis of the obtained Fipronil shows a new polymorph which is designated as 'G' form.

Example-3

Fipronil (15 gm) (prepared by oxidation of thiopyrazole using methylene dichloride (MDC) as a solvent and m-chlorb perbenzoic acid as a oxidizing agent, purity=78.86%, thiopyrazole=15.81%, fipronil sulfone=4.28%) was dissolved in 300 ml. of methylene dichloride (MDC). A column was prepared using 150 gm of Silica (60-120 mesh) using MDC as a solvent. A clear solution of Fipronil was added into the column and elution was done with MDC solvent at ambient temperature. Different products as per bands were separated and TLC analysis was carried out. MDC cut containing Fipronil was conentrated at 30-35° C. under vacuum and the product was isolated. The obtained Fipronil product shows 99.37% purity. XRD analysis of the obtined Fipronil shows a new polymorph which is designated as 'G' form.

Example 4

Preparation of Fipronil Form XI 100 gms of fipronil 'G' form (prepared as per example 1 or 2 or 3) was heated at 140 deg C. to obtain 62 g of crystalline fipronil form with 97.6% chemical purity by weight. The XRD analysis shows new crystalline polymorphic form which is designated as "XI" form of fipronil.

Example 5

Preparation of Fipronil Form X 12 gms of fipronil polymorhic form "XI" with a purity of 97.6% by weight (prepared as per example 4) was taken in a 30 ml mixture of ethyl acetate & chlorobenzene (70:30, v/v). The mixture was heated to about 75-80 deg C. until all the material was completely dissolved. The heating was discontinued after 60 minutes. The crystalline form was obtained by evaporating the solvent to dryness and further drying the solids at about 60 deg C. for 8-10 hrs. The isolated solid was then subjected to XRD analysis. The XRD analysis shows new crystalline polymorphic form which is designated as 'X' form of fipronil.

Example 6

Spray Solution

| FIPRONIL 5% SC | | |
|---|---|---|
| CHEMICALS | | Wt % |
| Fipronil (form G) | Active ingredient | 5.00 |
| Sunflower oil | Penetrating agent | 5.00 |

-continued

| FIPRONIL 5% SC | | |
|---|---|---|
| CHEMICALS | | Wt % |
| Techo SC 101 | Wetting agent | 4.00 |
| Dispertox SC 606 | Dispersing agent | 4.00 |
| DC 2210 | Defoamer | 1.00 |
| Proxel GXL | Biocide | 0.50 |
| Xanthan Gum | Thickening agent | 0.40 |
| Di-ethlyene glycol | Antifreezing agent | 1.20 |
| Deionised Water | | 78.90 |
| Total | | 100.00 |

Example-7

Water Dispersible Granules

| FIPRONIL 80 WG | | |
|---|---|---|
| CHEMICALS | | WT % |
| Fipronil Technical polymorph | Active ingredient | 80.00 |
| Sapcomar HR | Wetting agent | 4.00 |
| TAMOL FBPP | Dispersing agent | 5.00 |
| Sodium lauryl sulphate | Dispersing agent | 5.00 |
| Sodium lingo sulphonate | Binder | 4.00 |
| PEG400 | Disintegrating agent | 2.00 |
| Total | | 100.00 |

Example-8

Gel

Fipronil 0.05% Gel

| CHEMICALS | | WT % |
|---|---|---|
| Fipronil Technical polymorph | Active ingredient | 0.05 |
| Methyl peraben | Preservative | 0.05 |
| Glycerine | Solvent | 10.00 |
| Xanthan gum | Thickening agent | 1.25 |
| Fructose | Sweetening agent | 44.00 |
| water | Filler | 44.65 |
| Total | | 100.00 |

Example-9

Non-Dispersible Granules

Fipronil 0.3 Granules

| RM | | Wt % |
|---|---|---|
| Fipronil Technical polymorph | Active ingredient | 0.300 |
| Silica 22S | Inert | 0.250 |
| Rhodamine B Base | Colour | 0.030 |
| Nonyl phenol ethoxylate 6 moles | Wetting agent | 0.250 |
| Diacetone alcohol | Solvent | 2.000 |
| River sand 16-30 mesh | Inert substrate | 97.170 |
| Total | | 100.000 |

The applicant craves leave to submit formal data to establish significant enhancement of efficacy (as required under section 3(d)).

While considerable emphasis has been placed herein on the specific features of the preferred embodiment, it will be appreciated that many additional features can be added and that many changes can be made in the preferred embodiment without departing from the principles of the invention. These and other changes in the preferred embodiment of the invention will be apparent to those skilled in the art from the disclosure herein, whereby it is to be distinctly understood that the foregoing descriptive matter is to be interpreted merely as illustrative of the invention and not as a limitation.

The invention claimed is:

1. A crystalline polymorphic form G of fipronil which, in an X-ray powder diffractogram at 25° C. shows of the following reflexes

| Peak No | 2theta (degrees) | d (Å) |
|---|---|---|
| 1 | 6.15 | 14.36 |
| 2 | 8.37 | 10.56 |
| 3 | 11.31 | 7.82 |
| 4 | 12.16 | 7.27 |
| 5 | 12.84 | 6.89 |
| 6 | 18.22 | 4.87 |
| 7 | 19.07 | 4.65 |
| 8 | 20.82 | 4.26 |
| 9 | 24.93 | 3.57 |
| 10 | 25.65 | 3.47 |
| 11 | 26.32 | 3.38 |
| 12 | 28.96 | 3.08. |

2. The crystalline polymorphic form G as claimed in claim 1 having fipronil content at least 98% by mass.

3. A process for the preparation of the crystalline polymorphic form G of fipronil as claimed in claim 1, said process comprising dissolving solid form of fipronil being different from the crystalline polymorphic form G in dichloromethane to obtain a mixture and subjecting the mixture to column chromatography followed by concentrating and vacuum drying at 30 to 35° C.

4. The process as claimed in claim 3, wherein the solid form of fipronil contains at least 81% of fipronil by mass.

5. A pesticidal composition comprising:
a pesticidally effective amount of a crystalline polymorphic form G of fipronil and at least one excipient;
wherein, the crystalline polymorphic form G of fipronil in an X-ray powder diffractogram at 25° C., shows the following reflexes:

| Peak No | 2theta (degrees) | d (Å) |
|---|---|---|
| 1 | 6.15 | 14.36 |
| 2 | 8.37 | 10.56 |
| 3 | 11.31 | 7.82 |
| 4 | 12.16 | 7.27 |
| 5 | 12.84 | 6.89 |
| 6 | 18.22 | 4.87 |
| 7 | 19.07 | 4.65 |
| 8 | 20.82 | 4.26 |
| 9 | 24.93 | 3.57 |
| 10 | 25.65 | 3.47 |
| 11 | 26.32 | 3.38 |
| 12 | 28.96 | 3.08. |

6. The pesticidal composition as claimed in claim 5 is in a form selected from the group consisting of spray, solution, gel, suspension, granules and powder.

7. A method for controlling pests; said method comprises contacting the pests or their food supply, habitat, breeding grounds or their locus with a pesticidally effective amount of a composition as claimed in claim 5.

8. A method for protecting a plant from infestation and attack by pests; said method comprises applying a pesticidally effective amount of a composition as claimed in claim 5 to at least one plant part selected from the group consisting of foliage and stem.

9. A method of protection of seeds; said method comprises contacting seeds with a pesticidally effective amount of a composition as claimed in claim 5.

* * * * *